United States Patent
Fernfors et al.

(10) Patent No.: US 7,345,215 B2
(45) Date of Patent: Mar. 18, 2008

(54) ABSORBENT PRODUCT WITH LOW FRICTION ZONE

(75) Inventors: Ingemar Fernfors, Mölndal (SE); Anna-Gerd Doverbo, Mölndal (SE); Eva Franzén, Lavettgatan (SE)

(73) Assignee: SCA Hygiene Products AB, Gothenburg (SE)

( * ) Notice: Subject to any disclaimer, the term of this patent is extended or adjusted under 35 U.S.C. 154(b) by 2 days.

(21) Appl. No.: 11/017,666

(22) Filed: Dec. 22, 2004

(65) Prior Publication Data

US 2005/0165375 A1 Jul. 28, 2005

Related U.S. Application Data

(60) Provisional application No. 60/530,988, filed on Dec. 22, 2003.

(51) Int. Cl.
*A61F 15/534* (2006.01)

(52) U.S. Cl. .................... 604/378; 128/891

(58) Field of Classification Search ........... 604/378, 604/381, 382, 385.08; 128/889, 890, 891, 128/892, 893, 894
See application file for complete search history.

(56) References Cited

U.S. PATENT DOCUMENTS

| | | | | |
|---|---|---|---|---|
| 882,357 A * | 3/1908 | Tietjen | ................... | 128/891 |
| 1,539,659 A * | 5/1925 | Fitzpatrick | ................... | 128/891 |
| 2,669,989 A * | 2/1954 | Shoucair | ................... | 128/893 |
| 2,943,623 A * | 7/1960 | Thompson | ................... | 128/893 |
| 3,260,261 A * | 7/1966 | Gallovich | ................... | 128/889 |
| 3,648,291 A * | 3/1972 | Pankers | ................... | 2/16 |
| 4,074,512 A * | 2/1978 | Matt | ................... | 57/210 |
| 4,908,026 A * | 3/1990 | Sukiennik et al. | ................... | 604/378 |
| 4,959,059 A * | 9/1990 | Eilender et al. | ................... | 604/358 |
| 5,019,064 A * | 5/1991 | Eilender | ................... | 604/378 |
| 5,123,113 A * | 6/1992 | Smith | ................... | 2/455 |
| 5,201,780 A * | 4/1993 | Dinsmoor et al. | ................... | 5/679 |
| 5,352,217 A * | 10/1994 | Curro | ................... | 604/378 |
| 5,590,420 A * | 1/1997 | Gunn | ................... | 2/69 |
| 5,674,214 A | 10/1997 | Visscher et al. | | |
| 5,716,351 A * | 2/1998 | Roe et al. | ................... | 604/385.21 |
| 5,787,523 A * | 8/1998 | Lindberg | ................... | 5/81.1 HS |
| 5,803,920 A * | 9/1998 | Gilman | ................... | 604/378 |
| 5,899,207 A * | 5/1999 | Scheinberg | ................... | 128/882 |
| 5,938,649 A | 8/1999 | Ducker et al. | | |
| 6,061,829 A * | 5/2000 | Gunn | ................... | 2/69 |
| 6,085,750 A * | 7/2000 | Majkutewicz | ................... | 128/846 |

(Continued)

FOREIGN PATENT DOCUMENTS

| | | |
|---|---|---|
| EP | 0 272 683 A2 | 6/1988 |
| EP | 0 692 263 A2 | 1/1996 |
| EP | 1 206 944 A1 | 5/2002 |
| WO | 01/24753 A1 | 4/2001 |

*Primary Examiner*—Tatyana Zalukaeva
*Assistant Examiner*—Paula L. Craig
(74) *Attorney, Agent, or Firm*—Buchanan Ingersoll & Rooney PC

(57) ABSTRACT

An absorbent product includes a backsheet, a topsheet and an absorbent core structure located therebetween, the core including a topsheet-facing surface which is fixedly attached to the topsheet. A low friction zone is arranged between the topsheet and the topsheet-facing surface in an area where said topsheet is not attached to the topsheet-facing surface, or a sheet is secured at a portion of its periphery to the topsheet and the low friction zone is placed above the topsheet. These arrangements alleviate skin damage.

23 Claims, 4 Drawing Sheets

U.S. PATENT DOCUMENTS

| | | | |
|---|---|---|---|
| 6,103,953 A * | 8/2000 | Cree et al. | 604/365 |
| 6,120,783 A * | 9/2000 | Roe et al. | 424/402 |
| 6,362,387 B1 * | 3/2002 | Carlson et al. | 602/41 |
| 6,486,379 B1 * | 11/2002 | Chen et al. | 604/378 |
| 6,613,955 B1 * | 9/2003 | Lindsay et al. | 604/378 |
| 6,673,982 B1 * | 1/2004 | Chen et al. | 604/378 |
| 6,916,967 B2 * | 7/2005 | Wright et al. | 602/42 |
| 7,087,806 B2 * | 8/2006 | Scheinberg et al. | 602/41 |
| 2002/0016579 A1 * | 2/2002 | Stenberg | 604/361 |
| 2002/0037678 A1 * | 3/2002 | Ohata | 442/328 |
| 2003/0082970 A1 * | 5/2003 | Moberg-Alehammar et al. | 442/123 |
| 2003/0083633 A1 | 5/2003 | Johnson | |
| 2003/0199841 A1 | 10/2003 | Ashton et al. | |

* cited by examiner

ABSORBENT PRODUCT WITH LOW FRICTION ZONE

CROSS-REFERENCE TO RELATED APPLICATIONS

The present application claims the benefit of U.S. Provisional Application No. 60/530,988, filed in the United States on Dec. 22, 2003, the entire contents of which are hereby expressly incorporated herein by reference.

FIELD OF THE INVENTION

The present invention relates to an absorbent product (absorbent article) for absorbing human exudate, such as a diaper, a sanitary napkin, an incontinence garment, an incontinence pad, a pant-type diaper, etc. In particular, the invention relates to an absorbent product of the disposable type and is particularly suitable for use in a disposable diaper, even more particularly for an infant or new-born baby diaper.

BACKGROUND TO THE INVENTION

Absorbent products of the aforementioned type are well known.

Many absorbent products are provided with means for ensuring a good fit and tight contact with the wearer's skin so as to prevent leakage. An example of such a product is for example U.S. Pat. No. 5,674,214, which discloses a sanitary napkin in which a separation member is provided which causes the liquid permeable topsheet to maintain contact with the wearer's skin when forces are exerted by the wearer's thighs tending to separate the napkin surface away from the wearer during movement. Due to this arrangement, only the edge portions of the core can therefore be attached to the topsheet.

One problem existing with absorbent products of this type, and in general, is that the wearer may suffer from damage in the form of sore patches (such as so-called "nappy-rash") or chafing on the skin as a result of the frictional movement of a wearer-facing surface of the absorbent product against the wearer's skin. This skin damage may present itself in several forms, at several different locations.

Bed sores are a typical result of the use of absorbent products, and are particularly prevalent in bedridden patients who must lie for long periods on such absorbent products.

Another area where damage to the skin can occur is with new born babies, where the remainder of the umbilical cord remains attached for up to a few weeks after birth until the navel has fully healed. The umbilical cord is particularly sensitive at the point where the cord remainder is attached to the body. When the baby wears a diaper, the cord remainder tends to be rubbed by the wearer-facing surface of the diaper which can cause skin damage, or the cord remainder can become frictionally engaged with the wearer-facing surface and is then dragged with this surface when the baby moves and/or when the baby is handled by an attendant (e.g. the parents). This can cause discomfort and again can lead to skin damage. Even when the baby has no clothing over this area, the rolling and turning movements of the baby against sheets or covers can cause the same effect.

Other areas of absorbent products being in frictional contact with the skin can cause similar problems during relative movement between the skin and the wearer-facing surface of the absorbent product.

One solution to the problem of bed sores has been given in for example WO-A-01/24753. This discloses making a hole through the layers of the absorbent product at the location where the bed sore or other sensitive area of the skin is located. However, this leads for example to loss of absorbent material for absorbing exudate and also to an increased risk of leakage of exudate either through the hole or as a result of the reduced amount of absorbent material remaining. Furthermore, there is no real protection against layers of clothing or bed sheets for example touching the sore skin areas through the hole.

Likewise, with umbilical cord remainders, a similar solution has been proposed by cutting away a section of the diaper (i.e. in a central waist section overlying the cord remainder) to form an opening so that the umbilical cord no longer contacts the wearer-facing surface of the diaper. However, when the baby has an article of clothing put over the diaper, the cord remainder can then become entangled in the clothing and similar damage can result. Also, the loss of absorbent material in that area is undesirable. The edge of the opening also produces additional problems in that it can be sharp and/or hard, and/or the umbilical cord remainder may become caught in the edge.

A further document dealing with avoiding sore areas of skin developing due to frictional contact with diapers is U.S. Pat. No. 5,938,649. This document discloses the use of a friction-reducing substance, such as aloe vera, in the form of a coating layer applied to the portion of the absorbent product which would otherwise directly contact the skin. A further document with such friction-reducing coating is EP-A-0 692 263, whereby a high molecular weight solid waxy substance is used.

OBJECTS AND SUMMARY

An object of the invention is therefore to reduce or eliminate the problem of skin damage or irritation caused by frictional contact and movement of the wearer-facing surface of an absorbent product with respect to the wearer's skin.

A further object of the invention is to reduce or eliminate the problem of damage to the umbilical cord remainder and pain or skin damage in the navel area as a result of the frictional contact of the cord remainder with the wearer-facing surface.

Further features of the invention will be apparent to the reader of this specification.

The invention is based on the idea that the user's skin is damaged because the skin or the navel (or cord remainder) rubs against the skin contacting surface of the absorbent product when the absorbent product moves relative to the user. To prevent this, the invention seeks to allow easy sliding movement between layers in an absorbent product. The invention uses the natural friction between the user's skin and the skin-contacting surface of the absorbent product to a beneficial effect, whereby the friction between the skin-contacting surface and the user's skin is higher than the friction between a layer in contact with the low friction material in the absorbent product. Thus, movement between the skin and the skin-contacting surface will be reduced or eliminated when the absorbent product moves relative to the user.

This specification uses the terminology "low friction material zone". The low friction requirement is to be understood as producing a low coefficient of friction between the low friction zone and the surface against which it is intended to move in frictional contact. The coefficient of friction is then reduced (due to movement between layers of the absorbent product instead of movement between the skin and skin-contacting surface of the product) compared to the coefficient of friction when the low friction zone is not present.

The coefficient of friction, with the low friction material zone in place, is then reduced by at least 20%, preferably at least 30%, more preferably at least 50%, and even more preferably at least 60%, and still more preferably by at least 80%, compared to an absorbent product structure without a low friction material zone in place.

For such evaluations of the level of the coefficient of friction, any standard test may be used and normal loads of 0.5 kg may be applied in these tests between the materials, and the results compared both when using and when not using the low friction material zone, since it is the relative values of the coefficient of friction which are important.

However, in order to give full details of a suitable test under which the coefficient of friction (i.e. friction coefficient) can be measured in order to check correspondence with the levels of the friction and the coefficient of friction mentioned and intended in regard to the present invention, a test for frictional measurement is described later in this application together with test results obtained on a variety of materials.

As will become apparent, the low friction zone may be formed by a low friction sheet of material, such as a polyethylene sheet, a polypropylene sheet or a low-friction nonwoven sheet (such as Novelin 380-18, produced by J. W. Suominen O Y, Finland, which is a thermobonded nonwoven comprising bicomponent fibres and having a surface weight for example of 18 g/m$^2$) inserted between the topsheet and the core, each of which may be of fibrous material. In this way it will be evident that the absorbent core, which may for example be a cellulosic fluff pulp core (optionally covered with a tissue wrap), and the top sheet which may be a polypropylene nonwoven material, will have a friction coefficient between the surfaces (e.g. under a load of 0.5 kg or higher) which is higher than the coefficient of friction which would be present between the layers when a layer of polyethylene is inserted between the core and the top sheet.

The percentage area of fixed attachment of the topsheet to the absorbent core structure has been specified in the claims. The percentage of fixed attachment in this regard should be understood to be the surface area of the topsheet-facing surface of the core structure which is attached to the topsheet without allowing any significant degree of movement between the topsheet and the absorbent core structure. Thus, over the area where the core is attached to the topsheet, the core and topsheet should act in a substantially unitary manner. Where adhesive, e.g. hot-melt adhesive, is used as the rigid attachment means and is applied (for example by being sprayed) on to the whole upper facing surface of the core whereafter the topsheet is then placed on to the adhesive, there will still be areas which are free of adhesive, but these areas are relatively small (i.e. between 0 cm to 1 cm in diameter around the actual adhesive locations) and thus the topsheet facing surface of the absorbent structure acts in a substantially unitary manner with the topsheet. Such would therefore constitute 100% area of attachment in accordance with the claims. A 50% area of fixed attachment would likewise be where an area of half of the core topsheet facing surface is not adhered at all to the topsheet, etc.

The claims also refer to a "peripheral region" of a further sheet. The peripheral region is thus a region extending up to a distance of 2 cm from the actual periphery, or in a preferred case up to a distance of 1.5 cm inward from the actual periphery or in a more preferred case up to a distance of 1 cm inward from the actual periphery.

BRIEF DESCRIPTION OF THE DRAWINGS

Embodiments of the invention will now be explained in more detail with reference to certain non-limiting embodiments thereof and with the aid of the accompanying drawings, in which.

DETAILED DESCRIPTION OF PREFERRED EMBODIMENTS

Figure 1:
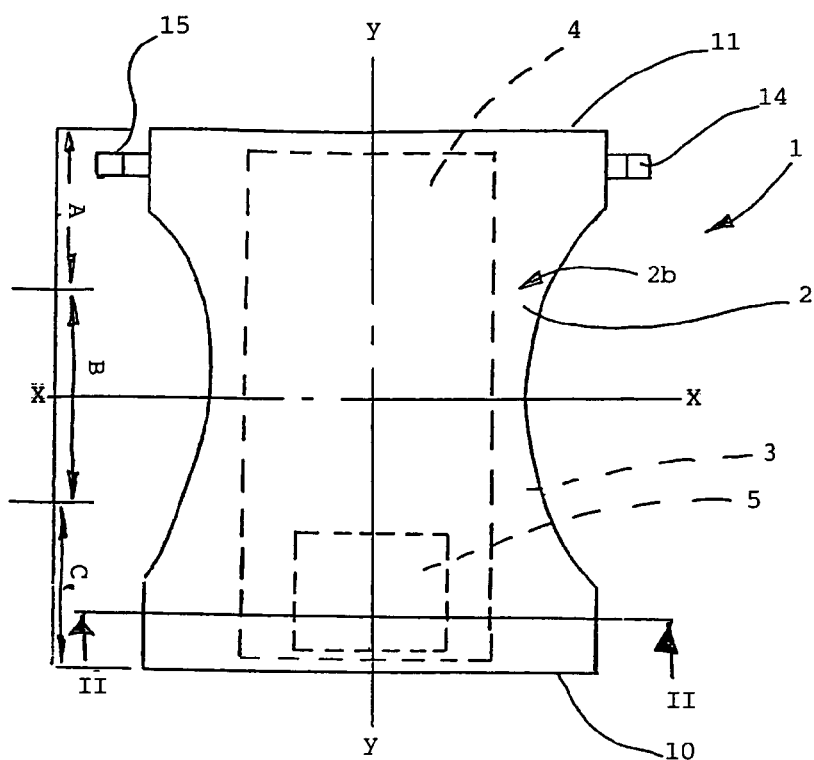
FIG. 1 shows an absorbent product in the form of a diaper in a laid flat configuration viewed from above on to the topsheet.

FIG. 1 shows an absorbent product 1. In FIG. 1, the absorbent product is in the form of a disposable diaper although the following explanation applies equally to other forms of absorbent product. The diaper shown in FIG. 1 is viewed from above on to the wearer-facing surface 2b of the liquid permeable topsheet 2. The diaper has a longitudinal centreline Y-Y, which passes substantially through the mid points of the end edges 10, 11. A lateral centreline X-X is also provided which is generally perpendicular to line Y-Y and positioned midway between the end edges 10 and 11.

The absorbent product also comprises a liquid impermeable backsheet 3 which is generally coextensive with the topsheet 2 and which is sealed to the topsheet at the respective peripheries of each of the sheets 2, 3. Lines of sealing are shown schematically at locations 12 and 13 in the cross-sectional view in FIG. 2 it being understood that lines of sealing 12 and 13 extend around the whole periphery outside the absorbent core structure 4 (see below).

Figure 2:
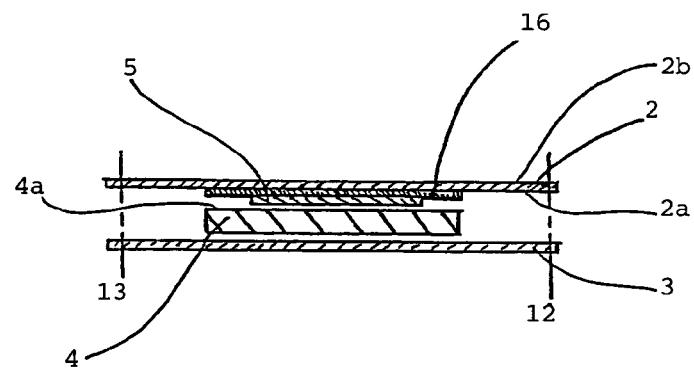
FIG. 2 shows a sectional view of the product in FIG. 1 along line II-II.

The absorbent product further comprises an absorbent core structure 4 which is enveloped between the topsheet 2 and the backsheet 3 (see also FIG. 2). The absorbent core structure may be formed in many ways and of many materials known in the art all of which are suitable for the product of the invention. The absorbent core structure may include a cellulose fluff layer with or without superabsorbent gelling materials. Likewise, the absorbent core structure may comprise several layers of the same or different materials, for example two cellulose fluff pulp materials. The absorbent core structure may additionally comprise layers for acquisition and distribution of bodily fluids.

A wrapping of tissue (not shown) may also be used in some cases to envelope one or more layers of the absorbent core structure.

Further, although the shape of the absorbent core structure is shown as rectangular it may be formed in many different shapes in all of its three dimensions.

The diaper also includes fastening means 14, 15 at one end of the product 1, such as reclosable fastening means of the adhesive type or of the hook and loop attachment type for example, which may be fastened to a cooperating surface on the back sheet 3 at the other end of the product. Other types of fastening are also possible. The invention may also comprise a pants-type diaper, in which case the provision of attachment means such as 14 and 15 may be omitted or included if the option of reclosure is to be provided.

The absorbent product is divided into three regions, each occupying approximately one third of the length of the product in the longitudinal direction. These regions may be regarded as the rear waist region A, the crotch region B and the front waist region C, whereby the front and rear waist portions are designed to be positioned against the wearer's waist and back portions during use.

Additional features may also be included such as leg and/or waist elastics and/or standing gathers, and/or other barrier arrangements of varying types, all of which are well known in the art of absorbent products.

FIG. 1 also shows the low friction material zone in the form of a sheet of material 5. As can be seen in FIG. 2, the material 5 is positioned between the top sheet 2 and the topsheet-facing surface of the absorbent core structure 4.

As can be seen in FIG. 1, the low friction zone formed by sheet 5 is preferably limited to a minor portion of the absorbent product, in this case it is limited to a region within the end third portion (i.e. front waist end portion C) of the product. However it is possible that a further low friction zone or zones may also be present.

Each of the low friction zones is preferably limited to a surface area of less than 50% of the absorbent product surface area (i.e. surface area of one side of top sheet 2). The low friction zone(s) may occupy even less than 50%, e.g. between 1% and 45%, and may typically lie in a range of 3% to 35% of the absorbent product surface area.

The low friction zone has been shown as centered laterally so that its longitudinal centreline lies generally aligned with the absorbent product longitudinal centreline Y-Y. However, the low friction zone may be positioned laterally to the left or right of line Y-Y if such is desired.

In the embodiment shown in FIG. 1, the location of the low friction zone is intended to take care of problems with umbilical cord remainders and thus it is positioned in the area of the product where the umbilical cord will be present when the diaper is fitted to the wearer. The actual area of the low friction material zone can also be adapted to take account of longer umbilical cord remainders.

The low friction material zone can be positioned right up to the sealing of the top sheet and back sheet at the end edge 10 and may of course extend into the zone B of the product if this is desired.

Although the low friction material zone is shown positioned where it will overly the umbilical cord remainder, the low friction zone may also be placed in other regions, for example two regions in the rear half of the diaper which generally align with the wearer's buttocks so as to reduce friction in that area.

The low friction material zone is shown as being rectangular in shape, but it will be apparent that other shapes than rectangular may also be used, such as oval, circular, star-shaped etc.

The sheet 5 is fixedly attached as shown in FIG. 2, to the core-facing surface 2a of the topsheet 2 by means of, for example, adhesive (e.g. hot melt adhesive) 16. Other methods of attachment may also be used such as welding or the like.

The topsheet-facing surface 4a of the absorbent core structure 4 is fixedly attached to the topsheet 2 over more than 10%, preferably between 10% and 60% of the surface 4a, and preferably all of the surface 4a, apart from where the low friction zone prevents said attachment. In the embodiment shown, the adhesive 16 extends on the topsheet 2 beyond the edges of the sheet 5 in all directions and can thus suitably be used to fixedly attach the topsheet 2 to the surface 4a.

The low friction material zone may be formed by a single flat sheet 5 of material as shown. Since the function of the sheet is to reduce friction, the sheet need not itself be absorbent or even permeable and thus very thin sheets of non-absorbent and impermeable or permeable polymeric film are particularly suitable. Whether the sheet should be permeable and/or absorbent depends on the location in the absorbent product. For example a polyethylene non-apertured film of between 10 and 25 µm thickness is suitable, although thicknesses up to 100 µm or more may be used if desired. The same thickness and surface weight ranges would also apply to a polypropylene sheet or a nonwoven sheet used in this manner. An apertured film can also be used as a low friction material.

The low friction zone may also be formed from several superposed sheets of material (not shown) if required, which may be useful in some situations depending on the surfaces against which the low friction material zone will move.

Although a sheet 5 of material is one embodiment of forming the low friction material zone, a low friction or friction-reducing substance may be used instead. Such substances are well known from the aforementioned documents U.S. Pat. No. 5,938,649 or EP-A-0 692 263. The low friction substance may be applied as a coating to the material against which friction should be reduced. For example in FIG. 2, the low friction substance may be applied between the topsheet 2 and the core structure 4, either to one or both of the surfaces 2a and/or 4a.

A low friction substance may also be used in addition to a sheet of material such as sheet 5, whereby sheet 5 may be made of a suitable material (such as nonwoven material) which can be coated and maintain a low friction substance coated thereon.

The absorbent core structure 4 may be fixedly attached at its lower side to the backsheet 3 in a manner not shown.

Figure 3:
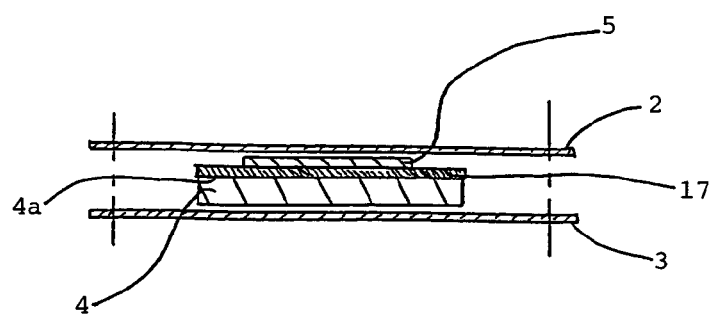
FIG. 3 shows a further embodiment of the invention in a sectional view similar to that in FIG. 2, but where the material constituting the low frictional material zone is fixedly attached to the absorbent core.

FIG. 3 shows a different embodiment, whereby the fixed attachment means, here an adhesive 17 (e.g. the same as adhesive 16), is placed on the upper surface 4a of the absorbent core structure 4. The topsheet 2 is then unattached to the low friction material zone, here again represented by sheet 5. The adhesive 17 may extend over the whole of the surface 4a or anywhere between about 10% and the whole area so that the topsheet 2 and the core structure 4 are attached to each other over at least 10% or more, as mentioned previously.

As will be apparent, a user's skin placed in contact with the topsheet 2 (i.e. surface 2b) when undergoing movement will have a relatively high friction with respect to sheet 2. However the topsheet has a relatively low friction against the core structure 4 as a result of the low friction material zone 5. Thus even under light loads of the skin against the topsheet 2, the topsheet 2 will be allowed to move with respect to the underlying core structure 4 (and the rest of the absorbent product) and thus skin chafing will be prevented or at least minimised. In the case of the umbilical cord remainder, this tends to have a very high frictional force against the topsheet due to the fibres and/or other rugosities in the topsheet layer, and thus remains easily held against the relatively high friction topsheet during body movement allowing while the topsheet layer can move at low friction over the underlying layer.

This movement of the topsheet against the core structure in this way is present basically because the layers of the absorbent product are not only flexible but also elongatable (especially where there is an excess of topsheet material, as is normal) as well as being slightly stretchable.

Figure 4:
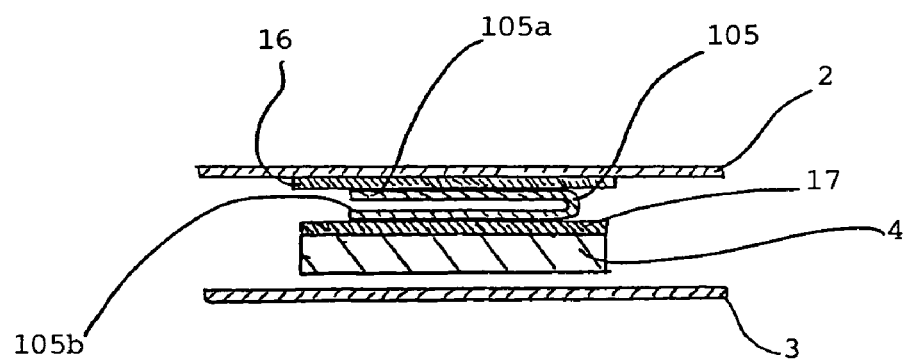
FIG. 4 shows a further embodiment of the invention in a sectional view similar to that in FIG. 2, but where the material constituting the low frictional material zone is fixedly attached to the absorbent core and to the topsheet.

FIG. 4 shows a further variation of the low friction material zone in the form of a rectangular sheet 105 of low friction material, similar to that in FIGS. 1 to 3, but which has been single folded at one edge thereof to form two overlying sheet halves 105a, 105b. Each of these sheet halves is attached to a respective one of the topsheet 2 and core structure 4. The attachment of the sheet half 105a may thus be the same as the attachment described with reference to FIG. 2 and the attachment of half 105b may be the same as the attachment described with reference to FIG. 3.

Again, the core structure 4 and the topsheet 2 are attached together by means of the adhesive 16 and 17 (as in FIGS. 2 and 3 respectively). It is of course possible that the adhesive 16 on the topsheet or the adhesive on the backsheet 17 does not extend beyond the low friction material zone to avoid using more adhesive than is required and/or to allow more flexibility.

As in the aforegoing embodiments, the core structure 4 may by affixed to the underlying back sheet 3 in any suitable known manner.

Although the topsheet 2 has been shown as a single layer in the various embodiments, it will be understood that the topsheet may comprise two, three or even more layers where said layers act in a unitary manner.

Figure 5:
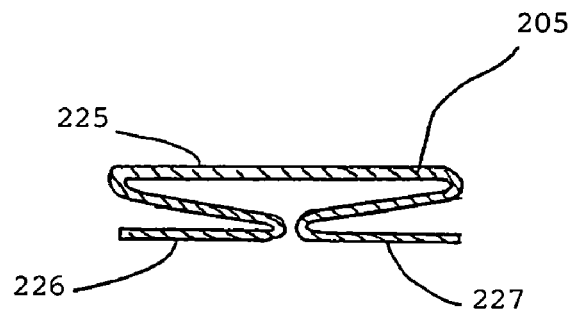
FIG. 5 shows a sectional view of a possible further embodiment of a sheet constituting the low frictional material zone.

FIG. 5 shows a still further variation on the sheet of material, which can be used to form the low friction material zone. In this embodiment, the sheet of material 205 is double folded at each side to thereby form the approximately the shape of a flattened omega. This sheet thus has an upper surface 225 and two lower surfaces 226, 227. Due to its particular shape, it is also suitable for fixing to the topsheet 2 and core structure 4 as shown in the previous embodiment of FIG. 4.

The embodiments of FIGS. 4 and 5 have the advantage that the friction levels can be even further reduced, since when movement of the topsheet occurs with respect to the absorbent core structure, the surfaces in contact with one another are both surfaces formed to provide low friction, whereas in the embodiments of FIGS. 1 to 3, only one of the surfaces is formed to provide low friction.

Figure 6:
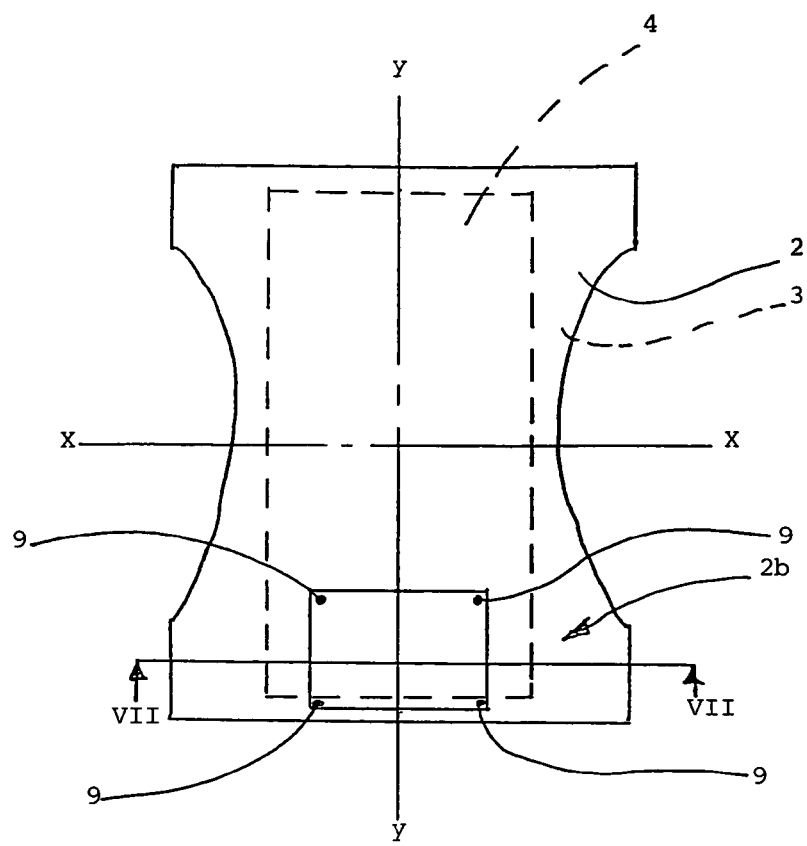
FIG. 6 shows a further embodiment of the invention, in which the material constituting the low frictional material zone is positioned on the outer, wearer-facing side of the topsheet.
Figure 7:
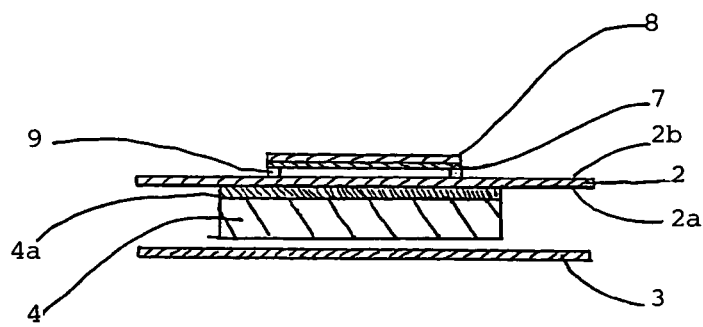
FIG. 7 shows a sectional view along line VII-VII in FIG. 6.
Figure 8:
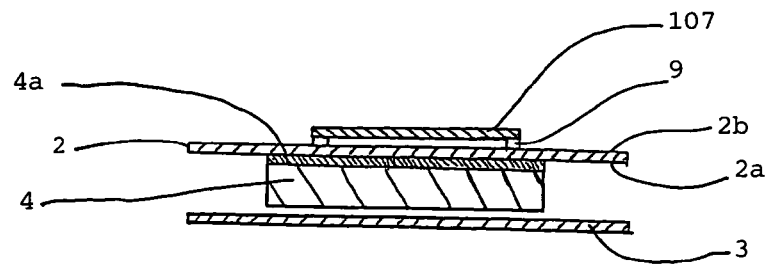
FIG. 8 shows a sectional view similar to that in FIG. 7, in which the material constituting the low frictional material zone is constituted by a single sheet.

In the embodiment of FIGS. 6, 7 and 8, the basic absorbent structure is the same as that shown in FIG. 1, with the exception of the low friction material zone which is placed on the wearer-facing surface 2b of the top sheet 2. In FIGS. 6 and 7, the low friction material zone is positioned below a further sheet 8, whereas in FIG. 8 the low friction material zone is constituted by a single sheet of material.

The low friction zone may be in the form of a sheet 7, 107, which may be formed similarly to the sheet 5, 105, 205 of the previous embodiments for example.

The absorbent core structure 4 is also attached at its upper surface 4a to the topsheet possibly over the entire area without interruption since the low friction material zone is located differently in this embodiment.

The further sheet 8 (when present, as in the embodiment of FIGS. 6 and 7), is attached (in this case by means of sheet 7 being formed as a laminate with further sheet 8, and where sheet 8 lies furthest from the topsheet upper surface 2b) over only a portion of its peripheral region, for example, at only four corner locations, to the topsheet. Only four (for example) fixed attachment locations 9 formed by adhesive, welding or other fixed attachment means, secure the further sheet 8 (and sheet 7) to the topsheet upper surface 2b (i.e. the wearer-facing surface 2b). The further sheet 8 should preferably not be stretched taut when being applied to the topsheet 2, and may also be slightly oversized (e.g. by 3 to 20 mm and preferably 3 to 10 mm) between its intended attachment points when compared to the length actually necessary to extend between attachment locations 9, so that the sheet 8 lies slack against the topsheet 2.

Figure 9A:
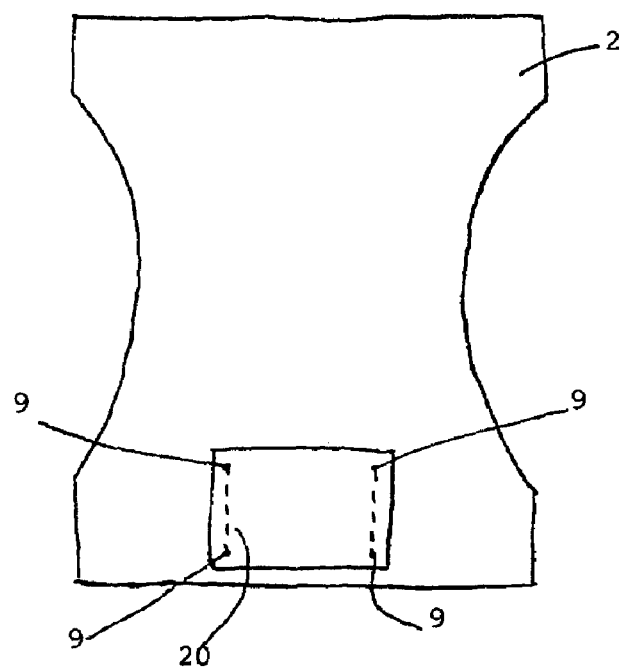
FIG. 9a shows a schematic view similar to that in FIG. 6, in which the attachment locations are supplemented by two laterally extending lines of attachment.
Figure 9B:
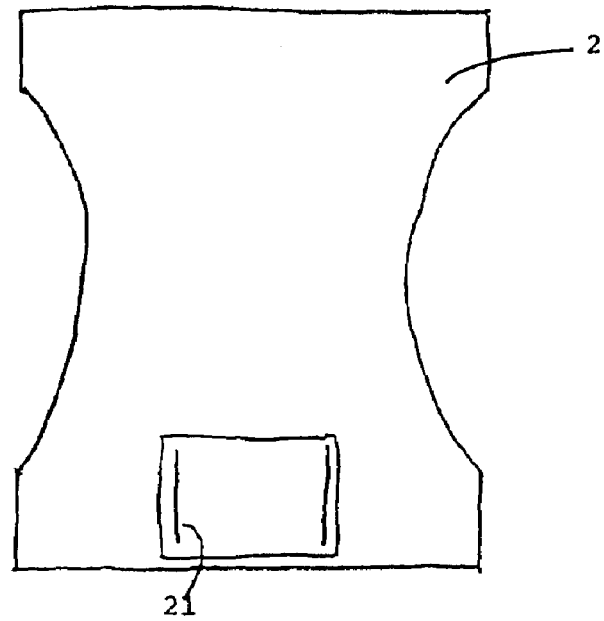
FIG. 9b shows a schematic view similar to that in FIG. 6, in which the attachment locations are replaced by two laterally extending lines of attachment.

As show in FIGS. 9a and 9b, The attachment locations 9 could be supplemented or replaced by two laterally extending lines of attachment (either continuous 21 or interrupted 20) between the corners at the peripheral region, whereby at least the majority of the length of the longitudinal peripheral edges are unattached.

In these configurations, with only partial attachment around the peripheral region of the further sheet 8 (or the peripheral region of the single layer shown in FIG. 8), the area of the further sheet 8 (or the single layer shown in FIG. 8) which is unattached to topsheet 2 is allowed to move somewhat with respect to the top sheet upper surface 2b. Since the further sheet 8 is also attached (e.g. by lamination or adhesive or by other means) to the low friction material zone formed by sheet 7, this movement of sheet 8 with respect to topsheet 2 takes place with a low frictional resistance. Thus the same effect as achieved with the previous embodiments is also achieved in this case.

Again, the embodiments have been shown in the form of a diaper and with a placement of the low friction zone such that the umbilical cord remainder is protected against chafing, although it will be appreciated that this arrangement may also be used on other locations in the diaper.

When used in the location shown in FIGS. 6 and 7, the sheet 8 may usefully be formed as a laminate with for example a nonwoven material (e.g. spunbonded, meltblown, etc.) on the upper side and a low friction material on the other side. Nonwoven materials are very suitable because they have a soft fibrous surface which is suitable for holding the umbilical cord remainder whilst the wearer is moving and thus creating a far higher frictional resistance to movement than is present between the low friction material zone and the layer against which it moves.

The general structural and shape variations which have been described in regard to the previous embodiments also apply to FIGS. 6 and 7, and can also apply to further absorbent products not depicted herein. Thus for example it will be clear that core structure 4 may be fixedly attached to the backsheet 3 by suitable means, and that the shape and location of the sheet 7 may vary considerably, etc.

In FIG. 8, the same basic structure is present as in FIGS. 6 and 7 with the exception that only a single sheet 107 of material is used on the wearer-facing surface 2b of the top sheet instead of two layers 7 and 8. Due to the relatively higher coefficient of friction present between the wearer's skin (in particular bed sore areas or the umbilical cord remainder) and the sheet of material 107, as compared to the friction between the sheet of material 107 and the topsheet wearer-facing surface 2b, the same friction-reducing effect as in previous embodiments is achieved. The friction between the wearer's skin and the sheet of material 107 is higher than that between sheet of material 107 and the topsheet 2, partly due to the skin's surface alone which is normally somewhat moist, while the umbilical cord remainder has a somewhat rough surface whereby the rough surface attaches itself very well to the fibres on one side of the sheet of material 107, especially when this sheet of material 107 is formed of fibrous material e.g. nonwoven material. In the area of bed sores, these will also exhibit a relatively high surface roughness and thus will act in a similar manner as the umbilical cord remainder with respect to the sheet 107.

The variations stated in connection with any of the previous embodiments also apply to the embodiment of FIG. 8.

As also depicted, there are preferably no further layers or sheets of material between the low friction material zone and the topsheet 2.

The single sheet of material 107 should be a low friction material. One example of a suitable material is the sheet of nonwoven Novelin 380-18 as described earlier. In this way, there is no need to provide any further treatment of the nonwoven material to achieve low friction.

It is useful to make the area of low friction material easily visible in the absorbent product. This also allows attendants using a new absorbent product to easily identify which area of the wearer's skin is intended to be protected from damage by that particular absorbent product. This is particularly useful in the embodiments where the low friction zone is in the form of a sheet or applied coating which is beneath the topsheet. A colour other than white (the colour white being understood to include off-white shades), such as blue or green, or another colour or colours, may be suitably used to identify the locations of the low friction material zones for the user. In particular, the colour of at least part of the low friction zone (preferably a part of the low friction zone which identifies the position of at least the border of the low friction zone) should preferably be different to that of the surrounding layers.

This colour can be part of the applied coating or the colour of the low friction sheet itself or the colour could be applied to the topsheet itself, possibly with suitable lettering to advise users of the intended purpose of the low friction material zone.

As mentioned above, a test for measuring the level of friction and the coefficient of friction between various materials or between a material and skin of a user (wearer) are disclosed in the following.

The friction for different combinations of materials, which have shown themselves to work when applied in/on a diaper in accordance with the invention, was measured according to the test method which is described below.

The principal for friction measurement of a combined material, i.e. between two specific materials, is to pull a sled having a sliding surface consisting of one of the materials in the combination over a fixed horizontally orientated surface consisting of the other material of the combination and thereby measure the force required to pull the sled.

The apparatus for friction measurement consists of a horizontally orientated friction board, a sled, a test-puller (for example an Instron) as well as a thin flexible wire between the test-puller and the sled. The test equipment further includes a pulley wheel applied to the friction board, whereby the wire runs around the pulley wheel so that the vertical movement of the test-puller is translated into a horizontal movement parallel to the friction board. The pulley wheel is made of hard plastic material and runs very easily and lightly around its support, whereby the increase of force caused by the pulley wheel friction is negligible during the friction measurement.

The sled consists of a rectangular steel plate with a surface of 40 cm$^2$. The underside of the sled, i.e. the side which is intended to slide against the friction board, is covered with an elastic coating, which is about 3 mm thick and intended to spread the pressure forces equally over the surface of the sled during the friction measurement. The weight of the sled is 500 grams (±5 grams). The edges of the sled, which during testing are intended to be orientated in the movement direction of the sled, are rounded. The thin wire is connected to the front edge of the sled, i.e. the edge of the sled which is intended to face forwards in the direction of movement when doing the test. The opposite end of the wire is connected, via the pulley wheel, to the test puller.

The friction board consists of a stable steel plate with a length of 50 cm and a width of 15 cm. The pulley wheel is arranged at the front edge of the steel plate, whereby the pulley wheel is positioned so that the wire runs along the movement line of the test-puller when the wire runs over the pulley wheel.

Test pieces of one of the materials of the combination were stamped out with a size of 65×100 mm intended to cover the underside of the sled. Test pieces with a size of 200 a 150 mm of the other material of the material combination to cover the friction board were also stamped out.

The materials were conditioned in 50±5% relative humidity (R.H.) and 23° C. for 4 hours before the test was performed.

During all handling of the test materials it is important to handle the test pieces as carefully and as little as possible so as to avoid finger prints, dust and the like, which could influence the measurement results.

It is furthermore important that the respective test piece is stamped out or cut out so that the friction measurement is performed in the intended direction on the respective test piece. Certain types of material such as for example many nonwoven materials exhibit different frictional characteristics in the machine direction and the cross direction. The test piece intended to be applied to the sled shall therefore be cut so that the long side (100 mm) of the test piece is parallel to the direction used for determining the friction coefficient and the test piece intended for the friction board shall also be cut with its long side (200 mm) parallel to the direction used for determining the friction coefficient.

The test piece intended to be applied to the sled was folded over the rounded front edge of the sled, whereafter the test piece was attached with tape to the top of the sled close to said front edge. The test piece was orientated with its long sides (100 mm) in the movement direction of the sled, whereby a small part of the test piece ended up behind the sled.

It is important to ensure that the test piece covers the whole underside of the sled and that it is smoothly and evenly applied to the sled.

The test piece intended for the friction board was applied essentially centered on the friction board, whereby the long sides (200 mm) of the test piece were arranged parallel to the movement direction of the sled. The test piece was fixed by means of tape along the short side of the test piece, which is attached to the back edge of the friction board, i.e. furthest from the pulley wheel on the friction board.

It is also important that this test piece is smoothly and evenly applied.

The wire was connected to the test-puller via the pulley wheel and was tensed to 0.05 N, whereafter the force of the test-puller was zeroed.

The test-puller was then started, as a result of which the sled was pulled over the friction board. The pulling speed was 100 mm/min and the total pulling length was 100 mm. Six samples of each material combination were tested.

The average force (F) which was needed to pull the sled across the friction board at a constant speed was measured. Further, the starting force was measured, i.e. the increased force which is required to make the sled move initially.

The sled was weighed and its weight (W) was determined with an accuracy of 0.03 g, whereby the weighing was done before the test piece was applied to the sled.

The dynamic friction coefficient of the material combination $\mu_D$ was calculated according to the formula $$\mu_D = F/(W \cdot 9.81).$$

The test method is a modified version of the testing method DIN 53 375.

Tests of the friction between nonwoven and skin were also performed.

During these tests, the same equipment was used as when making above-mentioned tests, but the friction board was replaced by the lower part of the arm of an adult test subject. The friction coefficient and the starting force were also measured in these tests.

EXAMPLE 1

In example 1 a situation was simulated, in which a friction layer of nonwoven is arranged between a liquid-permeable cover layer (topsheet) of an absorbent article and its absorption core (i.e. the absorbent core of the absorbent article), whereby sliding/movement is intended to occur between the cover layer and the friction layer.

The nonwoven material which simulated the cover layer of an absorbent article was constituted by a 17 gsm hydrophilic nonwoven material. The material has the manufacturing code 4WH05-01 017 H and is sold by BBA Nonwovens Sweden. The material is a conventional cover layer material used for absorbent articles.

The friction layer was constituted of the same nonwoven material as the cover layer.

The nonwoven material which simulated the cover layer of the article was tested on that side which was intended to be facing away from the user when the material is used as a cover layer on an absorbent article. For the friction layer, that side was tested which is normally intended to be facing towards the user when the nonwoven material is used as a cover layer on an absorbent article.

Both of the nonwoven materials were tested dry, and the materials moved against each other transverse to their respective machine directions. The term "machine direction" is intended to mean the direction in which the respective nonwoven material comes out from the nonwoven manufacturing machine and is normally rolled up on a roll.

The average force (F) between the layers was measured as 1.46 N and the starting force as 1.80 N. The friction coefficient ($\mu_D$) was then calculated as 0.30.

In example 1 the friction and the starting force were also measured between the nonwoven layer which simulated a liquid-permeable cover layer of an absorbent article, and skin. The friction was measured between the side of the nonwoven material which was intended to be orientated facing towards the user, and the underarm of the test subject.

The average force (F) between the nonwoven material and skin was measured as 1.80 N, and the starting force as 2.0 N, whereby the friction coefficient ($\mu_D$) was 0.37.

EXAMPLE 2

In example 2 the same material combination was tested in the same way as example 1 above, but the difference was that the tests were carried out using wet material and wet skin. The material layers and the skin were wetted with synthetic urine during the measurements.

The average force (F) between the layers was measured as 1.56 N and the starting force as 1.80 N. The friction coefficient ($\mu_D$) was then calculated as 0.32.

The average force (F) between the nonwoven and the skin was measured as 4.78 N and the starting force as 5.2 N. The friction coefficient ($\mu_D$) was as high as 0.97.

EXAMPLE 3

In example 3 the tests were carried out in the same way as in example 1 above, but one material was applied with the pull direction in line with the machine direction of the material and the other material with the pull direction transverse to the machine direction during the measurements.

The average force (F) between the layers was measured as 1.42 N and the starting force as 1.84 N. The friction coefficient ($\mu_D$) was 0.29.

During the measurement against skin, the movement direction of the nonwoven material was transverse to the machine direction of the material, but no difference could be seen compared to the measurements against skin in example 1.

EXAMPLE 4

In example 4 the same tests were performed in the same way as in example 3, but with the difference that the tests were carried out with wet material and wet skin.

The average force (F) between the layers was measured in this test as 1.57 N and the starting force as 1.75 N. The friction coefficient ($\mu_D$) was 0.32.

The friction coefficient between the layer representing the cover layer of an article and skin showed during measurement essentially the same values as in example 2 above.

In examples 1 to 4 above, embodiments are described which simulate a friction layer (i.e. a layer used to provide a low friction material zone as mentioned at other locations in this specification) of nonwoven which is arranged between the body-facing layer and the absorbent core of an absorbent article. The same friction values and starting forces would of course have been obtained if instead the friction layer had instead been placed above the cover layer. The difference would have been that the sides which were tested for the friction layer and the cover layer would have been upside down during each measurement, but the exact same combination would have been tested.

EXAMPLE 5

In example 5 a situation was simulated in which a friction layer (i.e. a layer used to provide a low friction material zone as mentioned at other locations in this specification) which is constituted by a three-dimensional perforated polyethylene, was arranged between a liquid permeable cover layer of an absorbent article and its absorption core (i.e. absorbent core), whereby sliding/movement is intended to occur between the cover layer and the friction layer.

The nonwoven material which simulated a cover layer of the article was constituted of the same nonwoven material as used in the examples 1 to 4 above, whereby the material was tested on the side which is intended to be facing towards the absorbent core.

The friction layer was constituted by a perforated polyethylene film from Tredgar Film Products as sold under the trade name White Aquidry Classic X 29893. The material type is commonly used as a liquid-permeable cover layer for absorbent articles, especially for articles intended to absorb menstruation liquids. The perforations were constituted by conical holes, due to which the film presents a three-dimensional structure.

The film is different on each side, whereby the side which is intended to be facing the user when the film is in use as the cover layer presents a soft and comfortable structure. The opposite surface of the film presents a noticeably rougher/scratchy surface which, with respect to comfort, in principal is impossible to use directly against the body of a user when the film is used as a cover layer on an absorbent article.

For the friction layer, that side was tested which is normally intended to be facing the user, i.e. the side which is soft.

Both material layers were tested dry, whereby the nonwoven material was tested transverse to the machine direction. The friction layer, i.e. the three-dimensional plastic film, presented the same characteristics independent of whether the movement between the material layers occurred in the machine direction of the material or transverse to the machine direction.

The average force (F) between the layers was measured as 0.95 N, and the starting force was 1.20 N. The friction coefficient ($\mu_D$) was calculated as 0.19.

The friction and the starting force between the nonwoven layer which simulated a liquid permeable cover layer of an absorbent article and skin was not measured in example 5 since the same conditions and material as in example 1 above are valid between the nonwoven material and the skin.

EXAMPLE 6

In example 6 the same tests were carried out in the same way as in example 5 above, but with the difference that the tests were carried out with wet material.

The average force (F) between the layers was measured as 1.0 N, and the starting force was 1.30 N. The friction coefficient ($\mu_D$) was calculated as 0.20.

The friction and the starting force against the skin were also not measured in this example, since corresponding measurements from example 2 are also valid for this example.

EXAMPLE 7

In example 7 a situation was simulated where a friction layer, which is constituted by a non-permeable polyethylene film, was arranged between a liquid-permeable cover layer of an absorbent article and its absorbent body, whereby sliding/movement are intended to occur between the cover layer and the friction layer.

The nonwoven material which simulated a cover layer of an article was constituted of the same nonwoven material as in examples 1 to 6 above, whereby the material was tested on the side which is intended to be facing the absorbent body.

The friction layer was constituted by an embossed polyethylene film from Trioplanex with the code Trioplanex 22 my ME 1148. The "female side" of the polyethylene film was tested.

Both the material layers were tested dry, whereby the nonwoven material was tested transverse to the machine direction. The friction layer, i.e. the plastic film, presented the same characteristics independent of whether the movement between the material layers occurs in the machine direction of the material or transverse to the machine direction.

The average force (F) between the layers was measured as 1.58 N, and the starting force was 1.98 N. The friction coefficient ($\mu_D$) was calculated as 0.32.

The friction and the starting force between the nonwoven layer which simulated a liquid-permeable cover layer of an absorbent article and skin was not measured in example 7 since the same conditions are valid as with example 1 above between nonwoven material and skin.

EXAMPLE 8

In example 8 the same tests were carried out in the same way as above in example 7, but with the difference that the tests were carried out with wet material.

The average force (F) between the layers was measured as 1.29 N, and the starting force was 1.44 N. The friction coefficient ($\mu_D$) was calculated as 0.26.

The friction and the starting force against skin were also not measured in this example, since corresponding measurements from example 2 are valid also in this example.

The following results were obtained:

| Example | Between material layers | | Between nonwoven and skin | |
|---|---|---|---|---|
| | Starting force (F) | Friction coefficient ($\mu_D$) | Starting force (F) | Friction coefficient ($\mu_D$) |
| 1 | 1.80 N | 0.30 | 2.0 N | 0.37 |
| 2 | 1.80 N | 0.32 | 5.2 N | 0.97 |
| 3 | 1.84 N | 0.29 | see example 1 | |
| 4 | 1.75 N | 0.32 | see example 2 | |
| 5 | 1.20 N | 0.19 | see example 1 | |
| 6 | 1.30 N | 0.20 | see example 2 | |
| 7 | 1.98 N | 0.32 | see example 1 | |
| 8 | 1.44 N | 0.26 | see example 2 | |

The tests show that all the measured friction layers (i.e. layers providing low friction material zones) present lower friction against a cover layer of an absorbent article than the friction which arises between the cover layer and a user's skin. Especially when the material layers and the skin are wet, the differences in friction are much larger.

Trials show that movements between a wearer's body and the absorbent article will preferably occur between the friction layer and the cover layer of the article. It is also a special advantage that the invention functions so well when the material and the skin are wet since the skin is substantially more sensitive to external influences when it is wet.

The measurements against the skin in the test above showed slightly larger variations than the measurements between different materials, since the determination of friction against a more undefined surface in the form of an underarm is simply not as accurate as against a fixed horizontal board.

Numerous variations of the invention can be made without departing from the scope of the claims. For example, the low friction zones may be applied in the umbilical cord area and the area of the buttocks or other sensitive region in the same absorbent product.

The low friction zones may also be used to reduce skin damage in sensitive skin areas at the location in the absorbent product where exudate exits the body, namely around the wearer's anus and/or genitalia. In such cases it may however be suitable to use absorbent materials for the low friction material zone or to apply coatings over a limited area. Non-absorbent materials can nevertheless also be used in these areas, for example by using a perforated polymeric film sheet.

The invention claimed is:

1. An absorbent product comprising a liquid-impermeable backsheet, a liquid-permeable topsheet including a core-facing surface and a wearer-facing surface, and an absorbent core structure located between said topsheet and said backsheet, said absorbent core structure including a topsheet-facing surface,
    wherein said topsheet-facing surface is fixedly attached to said topsheet over at least 10% of the surface area of said topsheet-facing surface,
    wherein a low friction material zone includes a low friction material arranged between said topsheet and said topsheet-facing surface in an area where said topsheet is unattached to said topsheet-facing surface,
    wherein said absorbent product is a disposable absorbent diaper including a waist region at either end thereof joined by a crotch region, and said low friction material zone is positioned at least partly in one of said waist regions,
    wherein said low friction material zone is limited to a surface area of less than 50% of said absorbent product surface area,
    wherein friction between the wearer-facing surface and a wearer's skin is higher than friction between a layer in contact with the low friction material and the low friction material in the absorbent product.

2. The absorbent product according to claim 1, wherein said low friction material comprises a sheet of material.

3. The absorbent product according to claim 2, wherein said sheet of material forming the low friction zone is single-folded at least at one edge.

4. The absorbent product according to claim 2, wherein said sheet of material forming the low friction zone is double-folded.

5. The absorbent product according to claim 2, wherein the low-friction sheet is permeable.

6. The absorbent product according to claim 2, wherein the low-friction sheet is absorbent.

7. The absorbent product according to claim 2, wherein the low-friction sheet has a thickness of 10 to 100 µm.

8. The absorbent product according to claim 2, wherein the low-friction sheet has a thickness of 10 to 25 µm.

9. The absorbent product according to claim 1, wherein said low friction material comprises an applied coating layer.

10. The absorbent product according to claim 1, wherein said low friction material comprises a sheet of material, said sheet of material being fixedly attached to said absorbent core structure and said topsheet.

11. The absorbent product according to claim 1, wherein said low friction material comprises a sheet of material, said sheet of material being fixedly attached to said absorbent core structure or said topsheet.

12. The absorbent product according to claim 1, wherein at least a portion of said low friction zone has a colour which is different to the surrounding colours in said absorbent product, so as to be easily visible in said product.

13. The absorbent product according to claim 1, wherein said low friction material zone is positioned in only one of said waist regions.

14. The absorbent product according to claim 1, wherein the low friction material zone is limited to a surface area of 1 to 45% of the absorbent product surface area.

15. The absorbent product according to claim 1, wherein the low friction material zone is limited to a surface area of 3 to 35% of the absorbent product surface area.

16. The absorbent product according to claim 1, wherein the low friction material comprises multiple superposed sheets.

17. The absorbent product according to claim 1, wherein at least a portion of the topsheet has a color which is different from the surrounding colors in the absorbent product, so as to be easily visible in the absorbent product and identify the location of the low friction material zone.

18. The absorbent product according to claim 1, wherein the low friction material zone comprises a longitudinal centerline and the absorbent product comprises a longitudinal centerline, wherein the low friction material zone is positioned to generally align the low friction material zone centerline and the absorbent product centerline.

19. The absorbent product according to claim 1, wherein the topsheet-facing surface is fixedly attached to the topsheet over 10 to 60% of the surface area of the topsheet-facing surface.

20. The absorbent product according to claim 1, wherein the topsheet-facing surface is fixedly attached to the topsheet over all of the surface area of the topsheet-facing surface, apart from where the low friction material zone prevents such attachment.

21. The absorbent product according to claim 1, wherein multiple low friction material zones are used.

22. The absorbent product according to claim 1, wherein the absorbent product is adapted such that a low friction material zone generally aligns with a wearer's navel region when the absorbent product is worn by the wearer.

23. An absorbent product comprising a liquid-impermeable backsheet, a liquid-permeable topsheet including a core-facing surface and a wearer-facing surface, and an absorbent core structure located between said topsheet and said backsheet, said absorbent core structure including a topsheet-facing surface,
    wherein said topsheet-facing surface is fixedly attached to said topsheet over at least 10% of the surface area of said topsheet-facing surface,
    wherein a low friction material zone includes a sheet of low friction material between said topsheet and said topsheet-facing surface in an area where said topsheet is unattached to said topsheet-facing surface,
    wherein said absorbent product is a disposable absorbent diaper including a waist region at either end thereof joined by a crotch region, and said low friction material zone is positioned at least partly in one of said waist regions,
    wherein friction between the wearer-facing surface and a wearer's skin is higher than friction between a layer in contact with the low friction material and the low friction material in the absorbent product.

* * * * *